US00PP16794P3

(12) United States Plant Patent
Lintott

(10) Patent No.: US PP16,794 P3
(45) Date of Patent: Jul. 11, 2006

(54) ***CHRYSANTHEMUM* PLANT NAMED 'CANARY SPIDER'**

(50) Latin Name: *Chrysanthemum morifolium*
Varietal Denomination: Canary Spider

(75) Inventor: Keith G. Lintott, Bognor Regis (GB)

(73) Assignee: Cleangro, Ltd, Chichester (GB)

( * ) Notice: Subject to any disclaimer, the term of this patent is extended or adjusted under 35 U.S.C. 154(b) by 48 days.

(21) Appl. No.: 11/055,278

(22) Filed: Feb. 9, 2005

(65) Prior Publication Data

US 2005/0183180 P1 Aug. 18, 2005

Related U.S. Application Data

(60) Provisional application No. 60/544,399, filed on Feb. 12, 2004.

(51) Int. Cl.
*A01H 5/00* (2006.01)

(52) U.S. Cl. ..... Plt./289

(58) Field of Classification Search ..... Plt./289
See application file for complete search history.

(56) References Cited

U.S. PATENT DOCUMENTS

PP7,586 P 7/1991 VandenBerg ..... Plt./78
PP8,804 P 6/1994 VandenBerg ..... Plt./78

*Primary Examiner*—Anne Marie Grunberg
*Assistant Examiner*—Annette H Para
(74) *Attorney, Agent, or Firm*—Winston & Strawn, LLP

(57) ABSTRACT

A new variety of *Chrysanthemum* plant named 'Canary Spider,' having a domed capitulum of bright yellow spider decorative flowers and a round shape.

1 Drawing Sheet

Latin name of the genus and species: Botanical classification: *Chrysanthemum morifolium.*

Variety denomination: The new *Chrysanthemum* variety denomination is 'Canary Spider.'

BACKGROUND OF THE INVENTION

The present invention comprises a new and distinct cultivar of *Chrysanthemum* botanically known as *Chrysanthemum morifolium,* and referred to by the variety name 'Canary Spider.'

'Canary Spider,' identified as 30860-0, originated from a cross made in a controlled breeding program in Chichester, West Sussex, United Kingdom. The female parent of the new *Chrysanthemum* variety is the variety known as 'Sarah' U.S. Plant Pat. No. 7,586. The male parent of the new *Chrysanthemum* variety is an undistributed, unpatented seedling identified as 'G26C23.' The new *Chrysanthemum* variety 'Canary Spider' has been asexually reproduced by vegetative cuttings in Chichester, West Sussex, United Kingdom and the distinguishing characteristics are retained through successive generations of asexual reproduction.

BRIEF SUMMARY OF THE INVENTION

'Canary Spider' is a garden type of *Chrysanthemum* plant variety having a domed, uniform capitulum of bright yellow spider decorative type of flowers.

Comparison with Female Parent

Plants of the new *Chrysanthemum* variety 'Canary Spider' are dissimilar to the parent variety 'Sarah' in plant habit and growth rate. In side-by-side comparisons in Chichester, West Sussex, United Kingdom, under commercial practice, plants of the new *Chrysanthemum* variety 'Canary Spider' differed from plants of the parent variety 'Sarah' in the following characteristics.

1. The new *Chrysanthemum* variety 'Canary Spider' produces yellow spider decorative flowers whereas the parent variety 'Sarah' produces bronze spider decorative flowers.
2. Plants of the new *Chrysanthemum* variety 'Canary Spider' have larger and shorter inflorescence than plants of the parent variety 'Sarah.'
3. Plants of the new *Chrysanthemum* variety 'Canary Spider' have a more domed and round shape than the more upright parent variety 'Sarah.'

Comparison with Male Parent

Plants of the new *Chrysanthemum* variety 'Canary Spider' are dissimilar to the parent variety 'G26C23' in plant habit and growth rate. In side-by-side comparisons in Chichester, West Sussex, United Kingdom, under commercial practice, plants of the new *Chrysanthemum* variety 'Canary Spider' differed from plants of the parent variety 'G26C23' in the following characteristics.

1. The new *Chrysanthemum* variety 'Canary Spider' produces yellow spider decorative flowers whereas the parent variety 'G26C23' produces pink quilled petal type decorative flowers.
2. Plants of the new *Chrysanthemum* variety 'Canary Spider' have a more rounded and domed habit than plants of the parent variety 'G26C23.'

Comparison with Other Variety

Plants of the new *Chrysanthemum* variety 'Canary Spider' are dissimilar to the variety 'Yellow Sarah,' U.S. Plant Pat. No. 8,804, in plant habit and growth rate. In side-by-side comparisons in Chichester, West Sussex, United Kingdom, under commercial practice, plants of the new *Chrysanthemum* variety 'Canary Spider' differed from plants of the variety 'Yellow Sarah' in the following characteristics.

1. The new *Chrysanthemum* variety 'Canary Spider' produces yellow spider decorative flowers whereas the variety 'Yellow Sarah' produces yellow quilled petal type decorative flowers.
2. Plants of the new *Chrysanthemum* variety 'Canary Spider' have a more rounded and domed habit than plants of the variety 'Yellow Sarah.'

BRIEF DESCRIPTION OF ILLUSTRATION

Typical specimens of the plant and flowers for the new *Chrysanthemum* variety 'Canary Spider' are shown in the accompanying digital photograph. The colors shown are as true as possible within the usual limits of this kind of illustration.

FIG. 1 is a whole plant view of the new *Chrysanthemum* variety 'Canary Spider' grown in a pot. The plant shown in the illustration is 63 days from the commencement of planting outdoors in mid-June.

DETAILED BOTANICAL DESCRIPTION

The following description of the new *Chrysanthemum* variety 'Canary Spider' is of plants grown outside, natural season, in Chichester, West Sussex, United Kingdom in the month of June. The variety has not been observed under all possible environmental conditions. The phenotype may vary significantly with variations in the environment such as temperature, length of day and light intensity, without any variance in genotype. The commercial classification of the new variety is a garden *Chrysanthemum.*

Plants of the new *Chrysanthemum* variety have been grown successfully under temperature conditions averaging about 50° F. at night and about 60° F. to 75° F. during the day under natural light conditions. The plants were grown outdoors in mid-June in 4 liter pots using loamless compost. No growth retardants were used. To produce a commercial product the plants may be pinched once with the center bud removed. The typical container size for commercial growth is 4 liters (8"). It has been observed that the shelf life of the new variety is about 26 days with a response time of about 9 weeks natural season. The new variety is suitable for growth in a temperature range of 50° F. to 75° F.

The new variety may be produced as a pot plant. The following description is with respect to a plant produced as garden pot plant. In the description of this new *Chrysanthemum* variety, color values have been taken from The Royal Horticultural Society Colour Chart (R.H.S.C.C.).

Plant

Plant type: Pot.
Habit: Domed/Round.
Height: 45 cm–50 cm.
Width: 45 cm–50 cm.
Branching characteristics: Free branching and spreading.
Length of lateral branches: 6 cm–11 cm.
Number of breaks from pinch: 7–11.
Stem color: 137A.
Response time: Near 63 days natural season.
Vigor: Medium.
Shelf life: Near 26 days.
Disease (susceptibility/resistance observed): None observed to date.
Pest (susceptibility/resistance observed): None observed to date.
Drought and temperature (susceptibility/resistance): None observed to date.
Growth retardant type and treatment: No treatment necessary.
The plants were grown for 9 weeks in natural season conditions.
Propagation:
*Type.*—Vegetative Propagation via Stem Cuttings.
*Time to rooting.*—12 days with soil temperatures of 70° F.
*Rooting habit.*—Fine and Fibrous.

Foliage

Number of leaves per lateral branch: 7–15.
Compound or single: Single.
Arrangement of leaves: Alternate.
*Shape of leaf.*—Typically 5 lobed ovate.
*Size of leaf.*—Width: 1.5 cm–2.5 cm. Length: 3 cm–4.5 cm.
*Leaf apex.*—Acute.
*Base.*—Obtuse.
*Attachment.*—Petioled.
*Aspect.*—Slightly undulating.
*Margin.*—Palmately lobed.
*Surface characteristics.*—Top: Slightly Pubescent. Bottom: Slightly Pubescent.
Petiole:
*Color.*—139C.
*Length.*—0.5 cm–0.7 cm.
Venation: Net. Prominent mid vein at underside.
*Color.*—Upper side: near 147B. Under side: near 147B.
Color:
*Mature leaf, upper side.*—Near 137A; under side: near 137B.
*Young leaf, upper side.*—Near 137A; under side: near 137B.

Flower

Flower appearance: Matte.
Flower type: Spider Decorative.
Flower form: Flat.
Flower shape: Round.
Flowering habit: Cyme.
Number of blossoms per branch: 7–12.
Inflorescence form: Corymbiform.
*Depth of fully expanded blossoms.*—1.5 cm–2 cm.
*Diameter of fully expanded blossoms.*—4.5 cm–6.0 cm.
Phyllaries:
*Number.*—15–20.
*Color.*—Near 138A.
*Length.*—0.5 cm–0.8 cm.
*Width.*—0.15 cm–0.3 cm.
*Texture/appearance.*—Slightly Pubescent/Dull.
Peduncle: Peduncle length is shortest at the terminal flower and progressively longer down the stem; longest length is on average 11 cm, shortest length is on average 6 cm.
*Length.*—6 cm–12 cm.
*Color.*—Near 138B.
*Surface.*—Pubescent.
*Habit.*—Slightly curving.
*Strength.*—Strong.
Ray florets:
*Form shape.*—Quilled.
*Texture/appearance.*—Shiny.
*Number per flower.*—140–150.
*Length.*—1.0 cm–3.7 cm; Width: 0.1 cm–0.3 cm.
*Apex.*—Rounded.

*Base.*—Tubular.
*Margin.*—Entire.
Disc florets: None observed.
Fragrance: Slight.
Flower bud (at onset of color):
*Length.*—0.6 cm–0.8 cm.
*Diameter.*—0.6 cm–1.0 cm.
*Form/shape.*—Ball shaped slightly flattened.
General flower color:
1. *Ray florets, upper side.*—Immature: near 2B. Mature: near 6B. Older/Fading: near 6B.
2. *Ray florets, under side.*—Immature: near 2B. Mature: near 6B. Older/Fading: near 6B.
3. *Bud.*—Near 139C.

Flower progression with age; Flowers hold the yellow color well with age.
The lastingness of blooms is about 26 days.

Reproductive Organs

Gynoecium present on Ray florets only.
Ray florets per individual flower:
*Pistil number.*—35–50 observed.
*Stigma color.*—Near 144C.
*Stigma shape.*—Forked.
*Style color.*—Near 9A.
*Style length.*—0.1 cm–0.3 cm.
Androecium not observed.
Fruit and seeds: None observed.

What is claimed is:

1. A new and distinct variety of *Chrysanthemum* plant, substantially as described and illustrated herein.

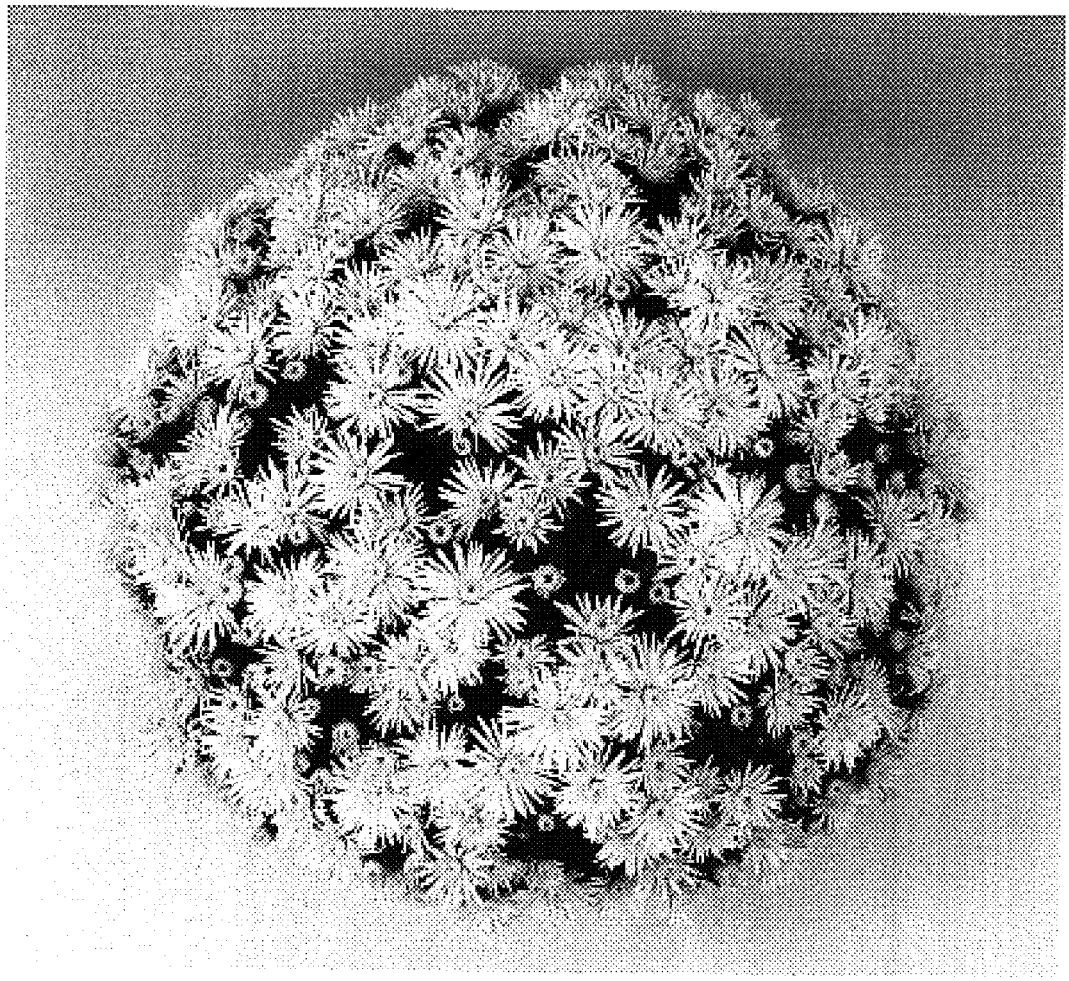

* * * * *